United States Patent [19]

Bharucha et al.

[11] Patent Number: 4,547,271

[45] Date of Patent: Oct. 15, 1985

[54] PROCESS FOR THE ELECTROCHEMICAL REDUCTION OF 7-KETOLITHOCHOLIC ACID TO URSODEOXYCHOLIC ACID

[75] Inventors: Kekhusroo R. Bharucha; Clarke E. Slemon, both of Toronto, Canada

[73] Assignee: Canada Packers Inc., Canada

[21] Appl. No.: 649,682

[22] Filed: Sep. 12, 1984

[51] Int. Cl.$^4$ ............................................. C25B 3/00
[52] U.S. Cl. .................................. 204/59 R; 204/75; 204/78
[58] Field of Search ...................... 204/59 R, 73 R, 78, 204/75

[56] References Cited

U.S. PATENT DOCUMENTS

| | | | |
|---|---|---|---|
| 2,356,596 | 8/1939 | Kramil et al. | 204/59 |
| 3,140,989 | 7/1964 | Kabasakalian et al. | 204/75 |
| 3,386,900 | 6/1968 | Slager | 204/75 |
| 3,506,549 | 4/1970 | Throop et al. | 204/75 |
| 3,720,694 | 3/1973 | Junghans | 204/59 R |
| 3,990,956 | 11/1976 | Junghans | 204/59 R |
| 4,050,998 | 9/1977 | Junghans | 204/59 R |
| 4,251,332 | 2/1981 | Ginsburg et al. | 204/75 |

FOREIGN PATENT DOCUMENTS

1372109  9/1963  France .
1391735  10/1963  France .

OTHER PUBLICATIONS

Holman et al., *Tetrahedron Letters*, "The Stereoselective Cathodic Reduction of Exo-Cyclic Double Bonds", No. 16, 1967, pp. 1553–1556.
James P. Colman, et al., *J. Chem. Soc.*, 1976, pp. 879–884, (J.C.S. Perkin II) "Electro-Organic Reactions, PVI, Stereoselective Cathodic Reduction of Unhindered Cyclic Ketones".
John W. Huffman et al., *J. Org. Chem.*, vol. 48, No. 9, 1983, pp. 1474–1479, "Metal-Ammonia Reduction of Cycloalkanones, A Revised Mechanism".
Robert A. Benkeser, et al., *J. of the Am. Chem. Soc.*, "The Selective Reduction of Aroatic Compounds to Dihydro or Tetrahydro Products by an Electrochemical Method", vol. 86, 1964, pp. 5272–5276.
Heinz W. Sternberg et al., *J. Am. Chem. Soc.*, "by Electrolytic Generation of Solvated Electrons and Reduction of the Benzene Ring in Ethanol Containing Hexamethylphosphoramide", vol. 89, Jan. 1967, pp. 186–187.
Throop et al., *J. Am. Chem. Soc.*, vol. 89, p. 4788, (1967).
Heinz W. Sternberg, et al., *J. Am. Chem. Soc.*, vol. 15, Jul. 1969, pp. 4191–4194, "by Electrolytically Generated Electrons".
J. P. Coleman, et al., *Chem. Communications*, "Stereoselective Electrochemical Reduction of Cyclic Ketones", 1971, pp. 104–105.

*Primary Examiner*—John F. Niebling
*Attorney, Agent, or Firm*—Bacon & Thomas

[57] ABSTRACT

A process for electrochemically reducing 7-ketolithocholic acid to ursodeoxycholic acid is disclosed. The process may be conducted alone or in conjunction with a simultaneous electrochemical oxidation of chenodeoxycholic acid to 7-ketolithocholic acid. Solvents for the electrochemical reaction which promote stereoselectivity to ursodeoxycholic acid are also disclosed.

16 Claims, No Drawings

PROCESS FOR THE ELECTROCHEMICAL REDUCTION OF 7-KETOLITHOCHOLIC ACID TO URSODEOXYCHOLIC ACID

BACKGROUND OF THE INVENTION

1. Technical Field of the Invention

This invention is directed to a process for the electrochemical reduction of 7-ketolithocholic acid to ursodeoxycholic acid (UDCA). The invention also concerns a process for the conversion of chenodeoxycholic acid (CDCA) to UDCA by the oxidation of CDCA to 7-ketolithocholic acid and simultaneous electrochemical reduction of 7-ketolithocholic acid to UDCA.

2. Description of the Prior Art

Chenodeoxycholic acid and its epimer ursodeoxycholic acid, are recognized as having the important medicinal activity of dissolving gallstones present in mammals. While chenodeoxycholic acid has recently been approved for use in the United States to dissolve gallstones, ursodeoxycholic acid is potentially more important since the dosage required to effectively dissolve gallstones is much less than that required of chenodeoxycholic acid. It, therefore, would be desirable to provide a process whereby ursodeoxycholic acid could be prepared in substantially pure form.

The asymmetrical reduction of hindered carbonyl compounds is usually strongly influenced by the preferred direction of approach of the reducing agent. In the case of 7-ketolithocholic acid, the oxidation product of chenodeoxycholic acid, that preferred approach gives back predominantly chenodeoxycholic acid, with only small amounts of ursodeoxycholic acid. For this reason, processes for reduction which give predominantly ursodeoxycholic acid are very important. The prior art contains disclosures of procedures for the production of ursodeoxycholic acid by the reduction of 7-ketolithocholic acid using sodium or potassium in alcohol solvents (see, e.g., French Pat. Nos. 1,391,735 and 1,372,109 and Chem. Ab. 87, 168276n), but use of these dangerous chemicals on the industrial scale is quite hazardous.

The stereoselective reduction of some steroidal nonconjugated ketones has been reported by Kobasakalian et al, J. Org. Chem. 26, 1738 (1961). Ketones at the 3, 6, 11, 12 and 17 positions afforded the equatorial isomer. Electrochemical reduction of certain ketones, including sterically hindered ketones, is treated in the work of Utley and his co-workers: Coleman et al, Chem. Commun. 1971 p. 104; Holman et al, Tetrahedron Letters, 1974 p. 1553; Coleman et al, J. Chem. Soc. Perkins II, 1976 p. 879; Holman et al, J. Chem. Soc. Perkins II, 1976 p. 884. In this work, sterically hindered ketones showed an increased tendency to give reduction to alkanes. Reduction in acidic solution also leads to the formation of methylene groups at the carbonyl location. Throop et al, J. Am. Chem. Soc., 89, p. 4790 (1967).

SUMMARY OF THE INVENTION

The subject invention is based upon the discovery that 7-ketolithocholic acid or its methyl ester or 3,7-diketocholanic acid can be electrochemically reduced to ursodeoxycholic acid or the corresponding methyl ester. In a preferred embodiment, the reduction is conducted in the presence of certain substances or mixtures of substances which because of their weak acidity and high polarity both promote the stereoselective reduction to ursodeoxycholic acid and improve the efficiency of the reduction. Such substances are dimethylsulfoxide, tetramethylurea, dimethylformamide, dimethylacetamide, N-methylpyrrollidone, 1,3-dimethyl-2-imidazolidinone, 1,3-dimethyl 3,4,5,6-tetrahydro-2(1H)-pyrimidinone, hexamethylphosphoric triamide and ethylenediamine. Simultaneously, because in every electrochemical system there must be an oxidation as well as a reduction, chenodeoxycholic acid can be oxidized to 7-ketolithocholic acid at the anode, thereby improving the overall efficiency of the process. These coupled reactions can be done in the presence or absence of stereoselective additives and in either the presence or absence of a porous membrane between the electrodes.

Accordingly, the invention comprises two processes for preparing ursodeoxycholic acid. In one aspect, the process comprises electrochemically reducing 7-ketolithocholic acid or 3,7-diketocholanic acid and their methyl esters to ursodeoxycholic acid and their methyl esters, preferably in the presence of a weakly acidic and highly polar substance which promotes the stereoselective reduction to UDCA. In a second aspect, the process comprises electro oxidizing chenodeoxycholic acid to predominantly 7-ketolithocholic acid with minor amounts of 3,7-diketocholanic acid and simultaneously electrochemically reducing these oxidation products to ursodeoxycholic acid with or without the presence of the promoter substance to promote stereoselectivity to UDCA.

Further details of the invention will be apparent to those of ordinary skill in the art upon review of the detailed description which follows.

DETAILED DESCRIPTION OF THE PREFERRED EMBODIMENTS

The electrochemical reduction of 7-ketolithocholic acid to ursodeoxycholic acid can be performed in any of the conventional electrolytic cells which have been proposed for electrochemical reduction of steroidal ketones. See, e.g., U.S. Pat. Nos. 3,140,989, 3,386,900 and 3,506,549. The cell contains a cathode and an anode disposed in a solution of electrolyte. The electrodes may or may not be separated by a semi-permeable membrance. Suitable materials for the membrance include inert polymeric materials such as polytetrafluoroethylene, cellulose acetate and various ion-exchange resins as well as porous glass.

The cathode may be made of any conducting material possessing a high hydrogen over-voltage, such as mercury, cadium, lead, zinc, nickel, iron, tin, ruthenized titanium and aluminum. The anode is selected from a variety of conductors which are difficulty oxidizable, such as carbon, nickel, iron, platinum, lead oxide and ruthenized titanium or other dimensionally stable anode materials. Mercury electrodes are particularly preferred as they promote quite significant stereoselective reduction to ursodeoxycholic acid even without the need of a stereoselective solvent.

Salts which are useful as the electrolyte are those containing a difficultly reducible cation, most preferably substituted ammonium salts such as tetraalkylammonium halides and hydroxides, e.g., tetramethylammonium hydroxide, tetraethylammonium hydroxide, tetramethylammonium chloride, tetraethylammonium chloride. Other electrolytes include alkali metal halides, e.g., lithium chloride, which is most preferably used in undivided electrochemical cells. When simultaneous oxidation and reduction is desired in either divided or undivided cells tetramethylammonium bromide or tetraethylammonium bromide may be included in the electrolytic mixture.

Solvents for the electrochemical cell include those conventionally used in electrochemical processes, i.e., aqueous-lower alkanol mixtures, e.g., methanol, ethanol as well as weakly acidic, dipolar additives: dimethylsulfoxide, tetramethylurea, dimethylformide, dimethylacetamide, N-methylpyrollidone, 1,3-dimethyl-2-imidazolidinone, 1,3-dimethyl-3,4,5,6-tetrahydro-2(1H)-pyrimidinone, hexamethylphosphoric triamide and ethylenediamine. This latter group of solvents are particularly effective in promoting stereoselectivity to ursodeoxycholic acid in the reduction of 7-ketolithocholic acid. Accordingly, in a preferred embodiment of the invention, these solvents are used to promote stereoselectivity and achieve high yields of ursodeoxycholic acid in relation to chenodeoxycholic acid. The use of these solvents are particularly effective when other than mercury electrodes are used in the electrochemical cell. Because mercury electrodes promote stereoselectivity to ursodeoxycholic acid, there is less of a need for stereoselective solvents.

The electrochemical process of the invention achieves reduction of 7-ketolithocholic acid or its methyl ester to ursodeoxycholic acid. 7-ketolithocholic acid is the predominant reaction product formed when chenodeoxycholic is oxidized. Minor amounts of 3,7-diketocholanic acid are also produced as oxidation reaction product. The electrochemical process of the invention also achieves reduction of this compound and its methyl ester when it is present as a by-product of the oxidation of chenodeoxycholic acid.

In a preferred embodiment of the invention, one of the weakly acidic dipolar additives, or a mixture thereof, most preferably hexamethylphosphoric triamide (HMPA) is used in an effective amount, as a component of the electrolyte system along with conventional solvents to promote stereoselectivity in the electrochemical reaction and to achieve a high yield of ursodeoxycholic acid as opposed to chenodeoxycholic acid. Typically from about 50–100%, by volume, based upon the volume of the electrolyte mixture, will be required to insure a high yield of ursodeoxycholic acid. Using the process of the invention, it is possible to obtain ratios as high as 5:1 or greater of ursodeoxycholic acid/chenodeoxycholic acid, from 7-ketolithocholic acid. In any case, the ratio is greater than 1:1 and usually greater than 3:1.

In a further embodiment of the invention, 7-ketolithocholic acid can be prepared in a divided cell by the simultaneous oxidation of chenodeoxycholic acid in the anode compartment while 7-ketolithocholic acid is being reduced by the same current to ursodeoxycholic acid at the cathode. In a further embodiment of this invention chenodeoxycholic acid or mixtures of chenodeoxycholic acid and ursodeoxycholic acid can be enriched in ursodeoxycholic acid in an undivided cell or in a divided cell with a common reservoir for catholyte and anolyte. Very weakly acidic, dipolar additives may or may not be added to insure stereoselectivity.

As previously stated, ursodeoxycholic acid is potentially an important compound for dissolving gallstones in the mammalian body. Treatment of patients with ursodeoxycholic acid would be essentially the same as current treatments with chenodeoxycholic acid, except that small and less frequent doses of the compound are necessary due to the superior activity of ursodeoxycholic acid over chenodeoxycholic acid. Typically, dosages between 8–10 mg/kg of body weight per day are considered the effective dosages for treating gallstones in human patients.

To further illustrate the invention, the following examples are provided, it being understood that their purpose is entirely illustrative and in no way intended to limit the scope of the invention.

EXAMPLE I

Oxidation of Chenodeoxycholic Acid to 7-Ketolithocholic Acid using Electrolytically Generated Bromine 10.0 g of pure CDCA were dissolved in 50 mL of methanol and 13 mL of deionized water (79% v/v methanol). Tetraethylammonium bromide (0.50 g) was added to give an approximate 0.04 M solution of electrolyte. An ECO ELECTROPREP (ELECTROPREP is a trademark of ECO INCORPORATED, 56 Rogers Street, Cambridge, MA 02142, U.S.A.) cell was assembled with a monel cathode, ruthenized titanium anode and a single large 0.062" thick viton spacer.

Electrolyzing, using a medium flow rate of 2 mL/sec and a constant current of 2 amperes, caused solid to precipitate in the reservoir. No bromine color appeared in the solution during the electrolysis. After significant product had been formed the electrolysis was stopped and the product filtered. The crude weight was 6.71 g of essentially pure white solid. The only impurity was a small amount of CDCA.

Chromatography of the mother liquors showed four tlc spots, chenodeoxycholic acid, 7-ketolithocholic acid, 3,7-cholanic acid and another byproduct.

EXAMPLE II

Reduction of 7-Ketolithocholic Acid in 60/40 HMPA-Ethanol

An ECO ELECTROPREP cell was assembled with two ruthenized titanium electrodes, a Teflon gasket and no membrane. In the reservoir was placed an electrolyte prepared from 0.76 g of lithium chloride dissolved in 36 mL of hexamethylphosphoric triamide (HMPA) and 24 mL of absolute ethanol (0.3 M solution). The substrate, 2.0 g, was dissolved and pumped through the cell while a current of 300 ma was applied. In total 160 coulombs were passed. The solvent turned yellow to orange-yellow. The electrolyte reaction solution was drained and the ethanol evaporated. The HMPA was largely removed by heating under high vacuum in a thin film evaporator. The residual oil was dissolved in 50 mL of 2N NaOH and let stand over the weekend. The alkaline solution was added dropwise to aqueous acid with a controlled pH of 2. Very little acid was required to maintain the pH 2 during the addition. The crystals were quite gelatinous and were difficult to filter. The recovered weight was 2.9 g but this by HPLC was only 39% bile acids, but the UDCA/CDCA ratio was 10:3 and the percent reduction was 72. By HPLC UDCA was 91% of the reduced material. By triturating with water an off white solid was reisolated, which by $C^{13}$ nmr analysis showed UDCA as 86% of the reduced products.

EXAMPLE III

Reduction of 7-Ketolithocholic Acid in DMSO-MeOH-Tetramethylammonium Hydroxide Solution at a Mercury Electrode and Isolation using Amberlyst A-26 Ion Exchange Resin The ECO ELECTROPREP mercury cell was assembled with a mercury pool cathode, a ruthenized titanium anode, two electrolyte chambers prepared using two expanded polytetrafluoroethylene (Teflon) gaskets separated by a sheet of dialysis membrane. The membrane is supported by Teflon strips running across the cell in the cathode chamber.

The electrolysis solution was prepared from 25 mL of 1.94 M tetramethylammonium hydroxide in methanol and 275 mL of dimethylsulfoxide (DMSO) combined and then dried over 3A molecular sieves. The cathode and anode reservoirs were each charged with 100 mL of this electrolyte and 2.01 g of 7-ketolithocholic acid dissolved in the catholyte. Initially 400 ma was passed through the cell but after delivering 200 coulombs, black solid appeared in the catholyte so the current was reduced to 100 ma. In total 2,568 coulombs were delivered over six hours. The catholyte was separated, filtered and the methanol removed on the rotary evaporator over a period of two hours at 50° C. Sodium hydroxide solution (2N, 5 mL) was added followed by 300 mL of water. The solution was added dropwise to a 140 mL column of Amberlyst A-26 resin in the hydroxide form, and then 500 mL of water was used to wash the column free of DMSO. The ion exchange column collected the yellow color from the reaction mixture in the top 0.5 cm of the resin. The aqueous elute was clear. Elution of the bile acids using 350 mL of 0.2 M $(NH_4)_2CO_3$ in 80% ethanolic solution removed the bile acids and the yellow color. The alcohol was evaporated to give a crude solid which was dissolved in 70 mL of water and 10 mL of 2N NaOH. This solution was added to an acid solution with a controlled pH of 2.0. The filtered dried product weight 1.72 g. HPLC-UDCA 53.9%, CDCA 14.1%, 7-ketolithocholic acid 32.0%, $C^{13}$ nmr UDCA 48%, CDCA 11%, 7-ketolithocholic acid 41%.

EXAMPLE IV

Reductive Equilibration of 7-Ketolithocholic Acid to a UDCA/CDCA Mixture

An ECO ELECTROPREP cell was assembled with a dialysis membrane as a diaphragm and a Teflon support to keep the membrane off the mercury surface. A viton gasket was used between the mercury electrode and the Teflon support. A polytetrafluoroethylene gasket was added to create the anode cell compartment. The electrolyte solution was placed in a common reservoir and circulated to both sides of the cells. For the initial reduction stage the reservoir contained a mixture of 60 mL of 20% aqueous Et$_4$NOH, 33 mL of deionized water and 200 mL of distilled methanol. The substrate was 3.0 g of 7-ketolithocholic acid. The anode was ruthenized titanium electrode. The current was between 600 ma and 1 amp. After three hours, the reduction had gone to completion. 3.0 g of tetramethylammonium bromide was added and the current passed (600 ma) for seven and one-half hours. The electrolysis was continued for twelve more hours. Tlc did not show any change in the UDCA/CDCA ratio; sample A was taken. The cell was cleaned, the solution filtered, and the pumps cleaned and reassembled. Three (3) grams more Et$_4$NBr was added and the electrolysis continued with a current of 600 ma for twelve more hours. Once again 3.0 g of tetramethylammoninum bromide was added and the equilibration run for twelve hours at which time the system was shut down. The aliquots A and B were purified and the recovered product analyzed by HPLC. The results are shown in the table.

| Sample | Bile Acids Identified % | % UDCA | % CDCA | % KLiCA | UDCA/CDCA | NMR UDCA/CDCA |
|---|---|---|---|---|---|---|
| A | 68.9 | 68.9 | 29 | 2 | 2.38 | 2.48 |
| B | 55.6 | 76.2 | 11.4 | 12.4 | 6.68 | 5.01 |

EXAMPLE V

Reduction of 7-Ketolithocholic Acid in HMPA and Isolation using Amberlyst A-26 Ion Exchange Resin The electrochemical cell was assembled with a monel nickel cathode, a ruthenized titanium anode, a Teflon gasket between the electrodes to provide a gap which constitutes the cell compartment, and no membrane. The electrolyte solution was 65.5 mg of anhydrous lithium chloride dissolved in 50 mL of hexamethylphosphoric triamide (HMPA). The substrate 2.06 g of 7-ketolithocholic acid was dissolved in this solution in the stirred reservoir and then pumped through the cell at ambient temperature. The rapid flow of electrolyte through the cell provided stirring in the cell. The initial current was 3 amperes, but gas evolution was so intense that it was reduced to 2 amperes. The reaction was considered over when 8,398 coulombs had been delivered. 5 mL of 2N sodium hydroxide was added to the reaction mixture along with 150 mL of water. This solution was added dropwise to a column containing about 200 mL of Amberlyst A-26 resin in the hydroxide form. When the entire reaction mixture had been run in, it was followed with 500 mL of water to wash the HMPA through the resin. The product mixture was eluted with 350 mL of 0.2 M ammonium carbonate in 80% ethanolic solution. Alcohol evaporation and acid precipitation gave 1.85 g of product. HPLC analysis:ursodeoxycholic acid 72.8%, chenodeoxycholic acid 17.3%, 7-ketolithocholic acid 9.8%; ursodeoxycholic acid/chenodeoxycholic acid=4.21.

EXAMPLE VI

Simultaneous Oxidation of Chenodeoxycholic Acid/and Reduction of 7-Ketolithocholic Acid A divided cell was assembled containing a cellulose acetate membrane, a mercury cathode, and a ruthenized titanium anode. The electrolyte was made up of 60 mL of 20% aqueous tetraethylammonium hydroxide, 32 mL of distilled, deionized water, 200 mL of HPLC grade methanol and sufficient solid phosphoric acid to bring the pH to 8.0. 2.0 g of 7-ketolithocholic acid was dissolved in 100 mL of this electrolyte and placed in the reservoir for the catholyte which was maintained at 65° C. 2.0 g of chenodeoxycholic acid was dissolved in another 100 mL of the above electrolyte and placed in the anolyte reservoir at 65° C. Both solutions were pumped through their respective half cells and a current of 400 ma applied. A total of 6,000 coulombs were delivered. Tlc of the catholyte showed essentially complete reduction to a mixture of ursodeoxycholic acid and chenodeoxycholic acid. Tlc of the anolyte showed that 7-ketolithocholic acid was the predominant product, there.

EXAMPLE VII

Reduction of 7-Ketolithocholic Acid in 97:3 1,3-Dimethyl-2-imidazolinone-Ethanol In an undivided flow-through cell with ruthenized titatium anode and cathode, 1.95 g of 7-ketolithocholic acid was dissolved in an electrolyte made from 0.65 g of lithium chloride, 60 mL of 1,3-dimethyl 2-imidazolidinone and 200 mL of absolute ethanol. The solution in both the cell and the reservoir was kept under nitrogen. Initially, current of up to 4 amperes were passed through the cell but polarization occurred and the current had to be reduced to 400 ma. Electrolysis was continued until 97 coulombs had been delivered. The solvent was removed under high vacuum, and the residue dissolved in 2N sodium hydroxide. The product was precipitated by adding this alkaline solution dropwise to acidic (pH 2.0) water. The recovery was 76.9%. The percent reduction was 36.8. The ratio of ursodeoxycholic acid to chenodeoxycholic acid was 1.45.

EXAMPLE VIII

Reduction of Methyl 7-Ketolithocholate at Mercury in Dimethylformamide

The mercury electrode was assembled using two expanded Teflon gaskets one in each of the anolyte and catholyte chambers. A diaphragm made of DARMAC (Grace Chemical) was used. The anode was ruthenized titanium. The electrolyte in both reservoirs was made up from 2.12 g of anhydrous lithium chloride, 0.55 g of hydroquinone as a proton source, and 500 mL of dimethylformamide which had been stored over 3A molecular sieves. The substrate, 0.4 g of methyl 7-ketolithocholate, was added to the catholyte reservoir along with some more 3A molecular sieves. The volume of the reservoirs was made up to 50 cc. exclusive of the volumes in the cell and the pumps. The reservoirs were purged with nitrogen and then with a steady flow through the cell electrolysis was begun with a current of between 300–625 ma and continued until 1,140 coulombs had passed. After further electrolysis the catholyte was burgundy. The catholyte was filtered and evaporated to a brown oil which was transferred to a 100 mL Erlenmeyer flask with 25 mL of methanol and 5 mL of water. To this was added 0.5 g of sodium hydroxide in 5 mL of water and the ester allowed to hydrolyze overnight. The acid was precipitated, collected and dried in the usual way. HPLC analysis indicated that the reduction was 56% complete (44% ketone). The percent UDCA was 44 and the percent CDCA was 12. The UDCA/CDCA ratio was 3.67. Analysis of the same sample by $C^{13}$ nmr indicated a UDCA/CDCA ratio of 4.17.

EXAMPLE IX

Reduction in the Dimethylsulfoxide-Methanol-Tetramethylammonium Hydroxide System The cell was assembled with a lead-plated monel electrode as cathode and a ruthenized titanium anode. The cell was undivided and contained just one Telfon gasket. A stock solution of electrolyte was made up from 25 mL of 1.94 M tetramethylammonium hydroxide in methanol and 475 mL of dimethylsulfoxide dried over 3A molecular sieves. The entire solution was stored over 3A molecular sieves and then 60 mL of electrolyte placed in the reservoir. 2.0 g of 7-ketolithocholic acid was dissolved therein, the flow was adjusted to a steady stream, and a constant current of 200 ma was established. 3960 coulombs were accumulated. When the cell was opened it could be seen that the monel sub-surface of the electrode was exposed. There were fine flakes of lead in the reservoir and pump. The filtrate was evaporated under high vacuum. The crude product was dissolved in 30 mL of methanol and 30 mL of 2N sodium hydroxide added. The solution was left at room temperature for five minutes and then the methanol evaporated. The product was precipitated with hydrochloric acid at pH 4.0 yielding 1.79 g after drying. The HPLC analysis indicated 45% reduction with a 37.6% yield of UDCA and 7.4% CDCA. The UDCA/CDCA ratio is 5.08. Analysis by $C^{13}$ nmr was qualitatively consistent with this ratio.

EXAMPLE X

Reduction of 7-Ketolithocholic Acid in an Undivided Cell using Tetramethylurea as Solvent An undivided cell containing a ruthenized titanium cathode and anode was connected to a reservoir containing 60 mL of 1,1,3,3-tetramethylurea (99%), 2.0 mL of absolute ethanol and 0.65 g of lithium chloride. The electrolyte was protected from air with a blanket of nitrogen. 1.95 g of 7-ketolithocholic acid was dissolved in the electrolyte and pumped through the cell. A current of 1 amp was passed for about twenty minutes until 1940 coulombs had accumulated. The solvent was removed under high vacuum, yielding an oil which was dissolved in 50 mL of 2N sodium hydroxide and added dropwise to acidified water giving a gum which solidified overnight in the refrigerator. The crude dry product weighed 1.7 g. HPLC analysis of this material indicated that the sample contained 77.94% identifiable bile acids. The conversion was 42% complete and the UDCA/CDCA ratio was at least 3.15.

EXAMPLE XI

Reduction of 7-Ketolithocholic Acid by Electrolysis In Distilled Ethylenediamine-Ethanol An undivided ECO ELECTROPREP cell was assembled with two ruthenized titanium electrodes. The cell thickness was equivalent to one Teflon gasket. The reservoir was charged with 50 mL of ethylenediamine, 0.85 g of lithium chloride, 2 mL of absolute ethanol and 1.95 g of 7-ketolithocholic acid. The reservoir was blanketed with nitrogen gas. With the electrolyte mixture pumping rapidly through the cell a current of 1 amp was applied. The solution which was initially cloudy, cleared and became slightly yellow. After sixty-five minutes 4091.3 coulombs had accumulated. The electrolysis was terminated and the reaction mixture evaporated under high vacuum. The residual thick yellow oil was mixed with 100 mL of toluene and distilled to dryness to remove traces of ethylenediamine as the azeotrope. The oil was put on the vacuum line and pumped down again. This material was dissolved in aqueous alkali and precipitated in acid to give after drying 1.722 g of bile acid mixture. HPLC analysis of this material gave a 92% of identifiable bile acids. The extent of reduction was 93% and the UDCA/CDCA ratio was 1.79 or 64% UDCA.

While the present invention has been described in terms of certain preferred embodiments, and exemplified with respect thereto, one skilled in the art will readily appreciate that various modifications, changes, omissions and substitutions may be made without departing from the spirit thereof. It is intended, therefore, that the present invention be limited solely by the scope of the following claims.

We claim:

1. A process for producing ursodeoxycholic acid or its methyl ester comprising electrochemical reducing 7-ketolithocholic acid or its methyl ester in a solution comprising an electrolyte and a weakly acid and highly polar solvent which promotes stereoselectivity to ursodeoxycholic acid such that the ratio of ursodexoycholic acid or its methyl ester to chenodeoxycholic acid or its methyl ester produced by the process is greater than 1:1.

2. The process as claimed in claim 1, wherein said solvent is a member selected from the group consisting of dimethylsulfoxide, tetramethlyurea, dimethylformamide, dimethylacetamide, N-methylpyrollidone, 1,3-dimethyl-2-imidazolidinone, 1,3-dimethyl-3,4,5,6-tetrahydro-2(1H)-pyrimidinone, hexamethylphosphoric triamide, ethylenediamine and mixtures thereof.

3. The process as claimed in claim 1, wherein said electrolyte is a member selected from the group consisting of alkyl substituted ammonium salts and alkali metal halides and mixtures thereof.

4. The process as claimed in claim 1, wherein said electrochemical reduction is performed in an undivided cell.

5. The process as claimed in claim 4, wherein said electrolyte is LiCl.

6. The process as claimed in claim 5, wherein said solvent is hexamethylphosphric triamide.

7. The process as claimed in claim 5, wherein said solvent is ethylenediamine.

8. The process as claimed in claim 1, wherein the electrochemical reduction is conducted in an electrochemical cell containing a mercury electrode.

9. The process as claimed in claim 1, wherein the 7-ketolithocholic acid is produced by electrochemically oxidizing chenodeoxycholic acid.

10. A process for producing ursodeoxycholic acid or its methyl ester comprising electrochemically reducing 7-ketolithocholic acid or its methyl ester, wherein the 7-ketolithocholic acid or its methyl ester is produced by electrochemically oxidizing chenodeoxycholic acid or its methyl ester and wherein said electrochemical oxidation of chenodeoxycholic acid or its methyl ester to 7-ketolithocholic acid or its methyl ester occurs simultaneously with said electrochemical reduction of 7-ketolithocholic acid or its methyl ester to ursodeoxycholic acid or its methyl ester.

11. The process as claimed in claim 10, wherein said simultaneous electrochemical oxidation and reduction is conducted in a solution comprising an electrolyte and a solvent which promotes stereoselectivity to ursodeoxycholic acid.

12. The process as claimed in claim 11, wherein said solvent is a member selected from the group consisting of dimethylsulfoxide, tetramethyl urea, dimethylformamide, dimethylacetamide, N-methylpyrollidone, 1,3-dimethyl-2-imidazolidinone, 1,3-dimethyl-3,4,5,6-tetrahydro-2(1H)-pyrimidinone, hexamethylphosphoric triamide and ethylenediamine.

13. The process as claimed in claim 11, wherein said electrolyte is a member selected from the group consisting of alkyl substituted ammonium salts, alkali metal halides and mixtures thereof.

14. The process as claimed in claim 10, wherein said simultaneous electrochemical oxidation and reduction is conducted in an electrochemical cell containing a mercury electrode.

15. The process as claimed in claim 10, wherein the ratio of ursodeoxycholic acid to chenodeoxycholic acid in the production of the electrochemical reaction is greater than 1:1.

16. The process as claimed in claim 15, wherein said ratio is greater than 3.1.

* * * * *

UNITED STATES PATENT AND TRADEMARK OFFICE
CERTIFICATE OF CORRECTION

PATENT NO. : 4,547,271
DATED : October 15, 1985
INVENTOR(S) : BHARUCHA et al

It is certified that error appears in the above-identified patent and that said Letters Patent is hereby corrected as shown below:

Column 2, lines 43 and 44, change "membrance" to -- membrane -- (two occurrences); line 52, change "difficulty" to -- difficultly --

Column 3, line 28, after "chenodeoxycholic" insert -- acid --

Column 5, line 54, change "cells" to -- cell --

Column 9, lines 14 and 15, change "ursodexoycholic" to -- ursodeoxycholic --.

Signed and Sealed this

Eighth Day of April 1986

[SEAL]

Attest:

DONALD J. QUIGG

Attesting Officer

Commissioner of Patents and Trademarks